United States Patent [19]

Reichenbach

[11] Patent Number: 5,715,946
[45] Date of Patent: Feb. 10, 1998

[54] METHOD AND APPARATUS FOR SORTING PARTICLES SUSPENDED IN A FLUID

[76] Inventor: Steven H. Reichenbach, 1747 31st Ave., San Francisco, Calif. 94122

[21] Appl. No.: 485,961

[22] Filed: Jun. 7, 1995

[51] Int. Cl.⁶ ........................................ B03B 5/66
[52] U.S. Cl. ........................ 209/156; 209/208; 209/210
[58] Field of Search ............................. 209/156, 210, 209/208, 422, 458, 459, 483, 488, 493, 494, 506, 507, 127.1, 131

[56] References Cited

U.S. PATENT DOCUMENTS

| | | |
|---|---|---|
| 2,715,860 | 8/1955 | Walters . |
| 3,899,427 | 8/1975 | Connelly . |
| 4,214,981 | 7/1980 | Giddings . |
| 4,250,026 | 2/1981 | Giddings . |
| 4,523,682 | 6/1985 | Barmatz et al. ............... 209/422 X |
| 4,737,268 | 4/1988 | Giddings . |
| 4,894,146 | 1/1990 | Giddings . |
| 5,039,426 | 8/1991 | Giddings . |
| 5,141,651 | 8/1992 | Giddings . |
| 5,193,688 | 3/1993 | Giddings . |
| 5,240,618 | 8/1993 | Caldwell et al. . |
| 5,290,401 | 3/1994 | Savisalo et al. . |

OTHER PUBLICATIONS

Cooney, C., "Centrifugation," Comprehensive Biotechnology, vol. 2, 1985, pp. 339–344.
Separation Methods, "Product Recovery," Chapter 6 pp. 111–122.

*Primary Examiner*—David H. Bollinger
*Attorney, Agent, or Firm*—Brinks Hofer Gilson & Lione

[57] ABSTRACT

An apparatus and method for dispersing particles suspended in a fluid by creating an obstacle field in a region of a conduit or receptacle and causing the fluid to flow through the conduit where the obstacle field has a configuration that causes the particles suspended in the fluid to disperse in a differential manner in a direction perpendicular to the flow of fluid as the fluid flows through the obstacle field.

65 Claims, 6 Drawing Sheets

SUSPENSION FLOW

METHOD AND APPARATUS FOR SORTING PARTICLES SUSPENDED IN A FLUID

FIELD OF THE INVENTION

The present invention relates to a method and apparatus for sorting particles suspended in a fluid and, more particularly, to a method and apparatus that employs an obstacle induced preferential dispersion process ("OIPD").

Numerous methods exist for concentrating particles in a fluid or separating particles from a fluid. Throughout this specification the term "particles" includes cells, cellular fragments or components, cell aggregates, very large proteins and solid particles composed of various substances such as precipitates, crystal particles, rock/sediment, for example, and the term "fluid" includes both liquids and gases. Often, these methods are used in the areas of processing blood components, fermentation processes and recovery of cells in biotechnological processes. Filtration is one method which excludes particles that are greater in size than the filter pore size or that are trapped in the filter matrix, i.e., depth filters. Filtration, however, is not easily implemented when the goal is to recover particles. In addition, filters often become clogged or caked which limits the usefulness of the filtration technique in continuous processes. Centrifugation is another method that requires the particles to have a different density or specific gravity than the fluid in which the particles are suspended. Adapting the centrifugation process for continuous processes is quite complex and costly. In addition, methods such as centrifugation, electrophoresis and sedimentation rely on unidirectional forces created by centripetal acceleration, electrostatic or electromagnetic fields or gravity respectively. Such unidirectional forces only allow particle shift in one direction.

Chromatography is another method that relies on the selective retardation or arrestation of some particles relative to the suspending flow. Some forms of industrial "scrubbers" separate particles by using elements that the particles "stick" or adhere to and thus trap the particles. For separating particles that have a higher density than the suspending fluid, inertial effects are often utilized. Such methods require the suspending fluid to undergo an acceleration or change in flow direction. The particles, with their higher inertia do not follow the flow and thus are separated from the fluid.

It is thus desirable to provide an apparatus and method for separating particles that is simple and inexpensive. In addition it is desirable to provide an apparatus and method for separating particles from a fluid that can be used in a continuous process and is substantially immune from clogging.

It is also desirable to provide an apparatus and method for separating particles from a fluid that does not require the particles to be buoyant or have a specific density different from the fluid.

It is also desirable to provide an apparatus and method for separating particles of different sizes without requiring the particles to have different specific gravities or settling velocities.

It is also desirable to provide an apparatus and method for collecting particles suspended in a fluid instead of trapping or excluding them.

SUMMARY OF THE INVENTION

According to a first aspect of the present invention, there is provided an apparatus for preferentially dispersing objects suspended in a fluid. The apparatus includes a conduit having an inlet, an outlet and an inner lumen extending from the inlet to the outlet. A non-uniform obstacle field is disposed in the inner lumen. The non-uniform field is configured to preferentially disperse the objects suspended in the fluid as the fluid flows through the obstacle field.

According to a second aspect of the present invention, there is provided a method for preferentially dispersing objects suspended in a fluid. The method includes providing a conduit having an inlet, an outlet and an inner lumen extending from the inlet to the outlet. A non-uniform obstacle field is located in a portion of the conduit. A fluid having objects suspended therein is injected through the conduit and the objects are collected at the output of the conduit.

According to a third aspect of the present invention, there is provided a method for separating particles from a particle entrained fluid. The method includes directing the fluid to flow through a conduit having an inlet, an outlet and an inner lumen extending from the inlet to the outlet and preferentially dispersing the particles in a direction perpendicular to the direction of fluid flow through the conduit to create a particle depleted region at the outlet of the conduit.

The invention itself, together with further objects and attendant advantages, will best be understood by reference to the following detailed description, taken in conjunction with the accompanying drawings.

DETAILED DESCRIPTION OF THE PRESENTLY PREFERRED EMBODIMENTS

Figure 1:
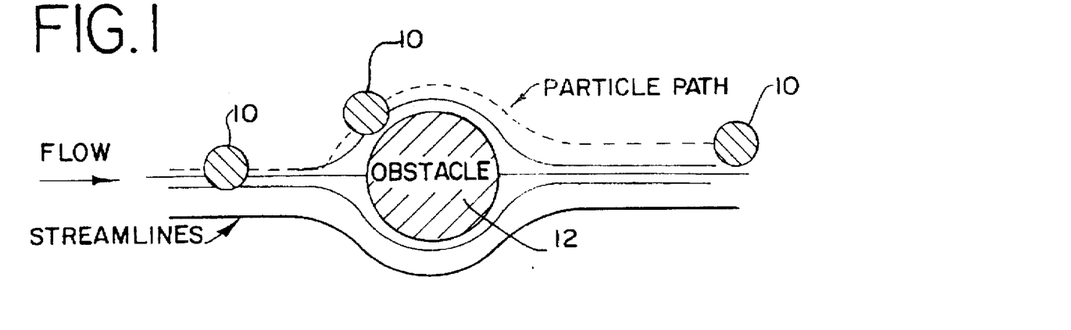
FIG. 1 illustrates in general the principle of OIPD.

FIG. 1 illustrates in general the principle of OIPD. When a particle 10 carried by a fluid encounters an obstacle 12, it is displaced in a direction perpendicular to the flow of the suspending fluid. As shown, a cylindrical obstacle 12 having its longitudinal axis perpendicular to the direction of fluid flow causes a particle 10 which encounters the obstacle 12 to be shifted or displaced in a direction perpendicular to the overall flow direction. The magnitude of the shift is dependent upon several factors which will be described in detail.

The preferred embodiments of the present invention shown in FIGS. 5–20 employ an obstacle field through which a fluid having particles suspended therein is passed. The obstacle field causes a preferential dispersion or migration of the particles so that they are separated from the fluid. In particular, a non-uniform obstacle field has a spatial density that varies in a given direction. For example, consider a flow along an X axis through a field of obstacles whose spatial density increases in the Y direction, i.e., there are more obstacles as one travels in the +Y direction. When a particle encounters an obstacle it is shifted in either the +Y or −Y direction relative to the flow. If the particle is shifted in the +Y direction there is an increased probability of encountering another obstacle and being shifted back to its original path. If the particle is shifted in the −Y direction, there is a decreased probability of the particle encountering an obstacle and being shifted back to its original path. Thus, the particles will tend to migrate in the −Y direction. This migration is referred to as obstacle induced preferential dispersion (OIPD). In addition, the magnitude of the particle path shift from a single obstacle is a function of particle size and thus the rate of particle migration will also be a function of particle size.

A discussion of the theory upon which it is believed that an obstacle field can produce this preferred dispersion will now be described.

Figure 1A:
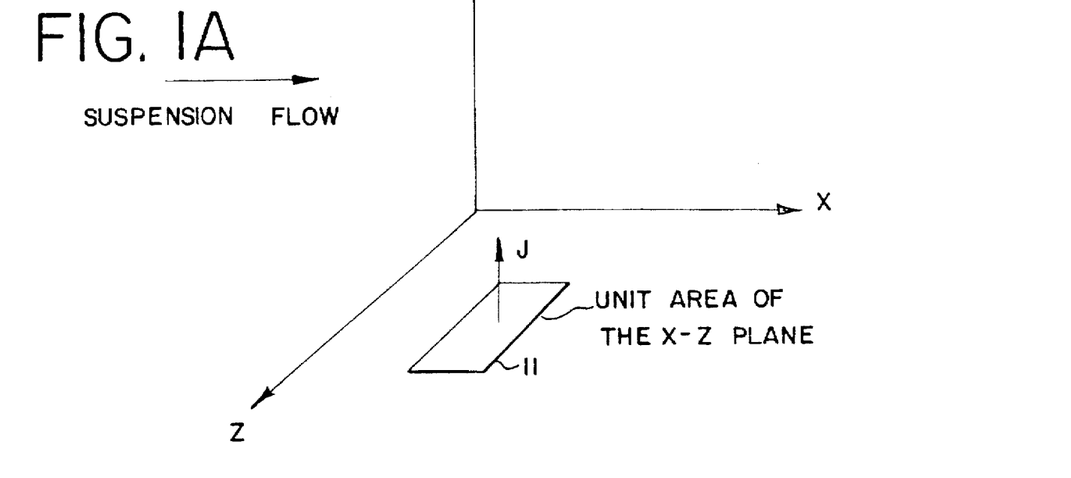
FIG. 1A illustrates the definition of the y component of particle flux, J.

Certain assumptions must be made in order to define the flux of particles, J, perpendicular to the fluid. Particle flux is the rate at which particles pass through a surface per unit area of that surface. FIG. 1A illustrates the definition of flux, J. In particular, the particle flux in the Y direction is equal to the number of particles that pass through the unit area 11 per second. The assumptions made merely help define the flux mathematically but they do not need to be present in order for OIPD to operate successfully. First it is assumed that a dilute suspension of particles is present so that the movement of the particles does not influence the overall suspending fluid flow and that particles do not interact with one another. Second, it is assumed that the obstacle field is also dilute so that a particle encounters only one obstacle at a time. It is also assumed that there is fore and aft symmetry in the flow field around an obstacle and that particles follow the streamlines unless they interact with an obstacle. In addition, each particle that encounters an obstacle is shifted perpendicular to the flow direction, to a position h from the obstacle centerline which is parallel to the flow direction. (See FIG. 1) A particle will encounter an obstacle if upstream of the obstacle it is within the distance h of the obstacle centerline. Thus, if an obstacle is located between y=o and y=h upstream of the obstacle, it will be shifted to y=h downstream of the obstacle. Similarly, any particle located between y=o and y=−h upstream of the obstacle will be shifted to y=−h.

With these assumptions in place the net particle flux J in the y direction for a suspension flow in the x direction can be described by equation (1) below:

$$J = \frac{-h^3}{3}\left(2cu\frac{d\chi}{dy} + c\chi\frac{du}{dy} + u\chi\frac{dc}{dy}\right), \quad (1)$$

where c is the particle concentration, u is the velocity of the suspension and $\chi$ is the concentration of obstacles. Particle flux is what leads to particle separation in the OIPD process. As defined above, the flux is strongly dependent upon h so that by increasing h the OIPD separation is enhanced. As will be discussed in greater detail, h is dependent upon particle size which is one reason OIPD can be used effectively to separate particles of different size.

Many factors affect the amount of particle shift h resulting from a single obstacle including particle size and shape; obstacle size, orientation and shape; relative surface properties of the obstacle and particle; relative charge of the obstacle and particle; and the Reynolds number associated with the suspension flow over the obstacle. Obstacles with circular cross-sections, i.e. cylinders, are used in the present description; however, obstacles having non-circular cross-sections may also be used and may be advantageous for particular applications. A cylinder perpendicular to the flow will clearly shift particles. A long cylinder parallel to the flow will not shift particles because, generally, suspending flow stream lines do not approach the surface of the cylinder and thus the flow will not carry particles toward the obstacle where an interaction and consequent shift can occur.

The surface properties of the particle and obstacle can also influence the downstream shift of particles. If the two surfaces are philic, i.e. attracting, then the particle will tend to cling to the obstacle rolling or sliding along the back side of the obstacle and "detaching" closer to the centerline resulting in a smaller downstream particle shift. Phobic surfaces would have the opposite effect. If the particle carries a net electric charge, a repulsive force between the particle and obstacle would increase the shift created by an obstacle. If the obstacle and particle have opposite charges, the downstream shift would be diminished.

In addition, to the influence of h on the particle flux, the other terms in the above equation yield insight into the separation process. The first term in brackets is the driving force for OIPD, and is proportional to the obstacle concentration gradient in the y direction, $\partial\chi/\partial y$. A negative obstacle concentration gradient leads to flux in positive y direction (e.g., if the number of obstacles decrease in the y direction, then there is a tendency for particles to migrate in the y direction as they are carried in the x direction by the suspending fluid).

The second term in brackets shows a suspension velocity gradient in the y direction, $\partial u/\partial y$, (in the presence of obstacles) can also create a particle flux normal to the suspension flow. This is important to the design of the device used to implement the OIPD process because it is possible to have conditions where the velocity gradient has the opposite sign of the obstacle gradient, and therefore reduces the desirable particle flux. Generally the more obstacles you have the greater the "resistance" to flow, so if there is positive obstacle gradient in the y direction, then typically there will be a negative gradient in velocity in the y direction. Therefore, the velocity gradient will reduce the flux from the obstacle gradient. If the flow field is kept uniform, $\partial\chi/\partial y=0$, and the obstacle gradient remains, then there is no reduction in the flux. There are several ways to maintain more uniform flow even in the presence of an obstacle gradient. Among those include using the shape of the OIPD device to control flow velocity gradients and using spacers (surfaces to slow the flow) in the regions with lower obstacle concentration as will be described with reference to FIGS. 8–18. Of course, with a uniform obstacle concentration, the velocity gradient could drive the OIPD process.

The third term in the equation is a concentration driven dispersion or diffusion. This tends to counter the separation process so it must be considered when designing OIPD devices. This term also suggests that to achieve a highly concentrated effluent suspension along with a very dilute one, a device needs a large obstacle concentration gradient to dominate the particle flux.

The equation for particle flux shows OIPD is highly dependent on the particle shift, h, resulting from an obstacle. The influence of particle and obstacle size can be quantified by simplified analysis of the particle shift resulting from cylindrical obstacles perpendicular to the suspension flow. Assume that fluid flow around an obstacle is not influenced by other obstacles or the particles. Because most applications involve very small particles and obstacles, assume low Reynolds number flow, Re (this implies that the viscous forces are large compared to the inertial forces). Consider only physical contact between the particle and obstacle; ignore surface interaction, charge, localized hydrodynamic effects (i.e., particles follow fluid streamlines unless they physically contact an obstacle). These assumptions are not limits but instead are used to simplify the theoretical development. An exception to this is the low Reynolds number, at higher Re (Re>20 based on obstacle radius) unsteady vortex shedding for obstacles will probably create sufficient mixing to null the OIPD effect. Altering the shape of obstacles could stop unsteady shedding at higher Re. In addition, unsteady shedding will probably be reduced with more densely packed obstacles, however, higher Re most likely won't occur for the small obstacles used with particle suspensions like cells, etc.

Figure 2:
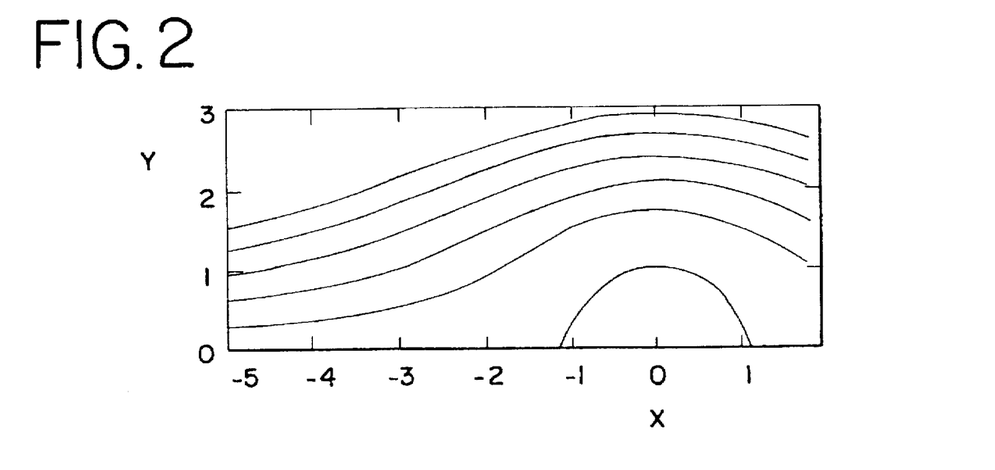
FIG. 2 illustrates the streamlines around an obstacle with a radius of one and a Reynolds number of 0.1. located at x=o, y=0.
Figure 3:
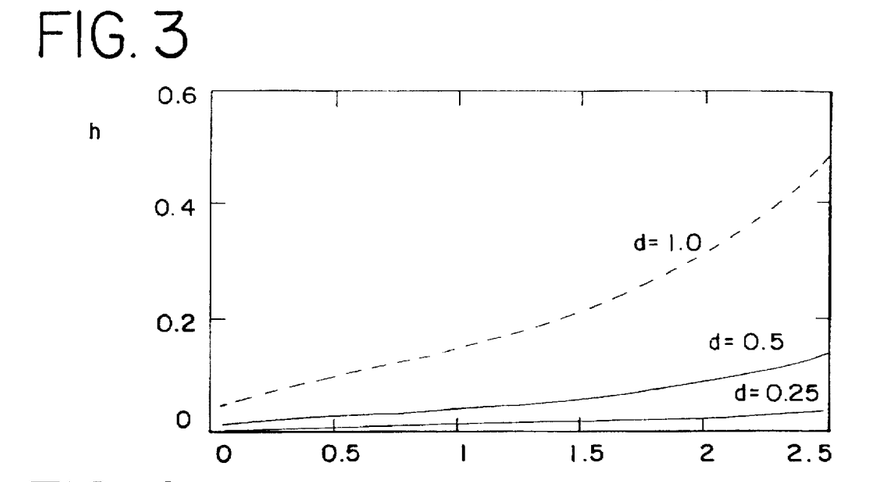
FIG. 3 is a graph illustrating the influence of particle size on h shown as a function of Re.
Figure 4:
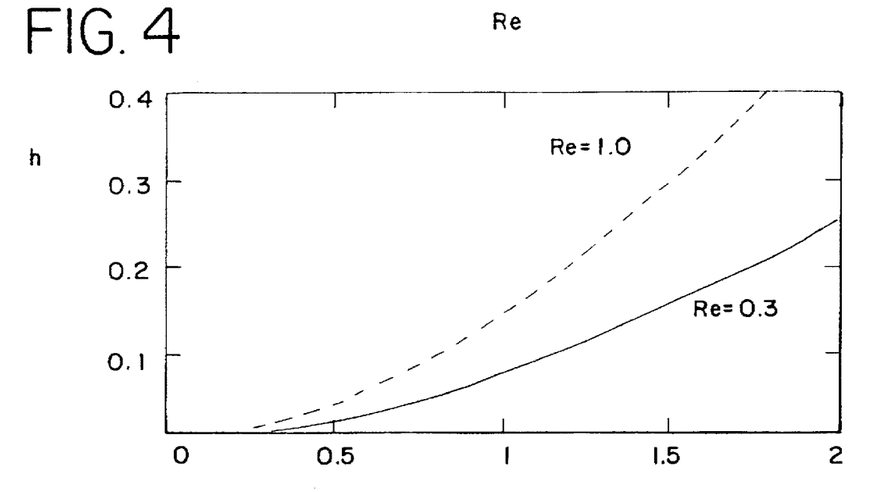
FIG. 4 is a graph illustrating the dependence of h on particle size.

With the above assumptions, the streamlines around an obstacle can be computed. FIG. 2 illustrates the streamlines around an obstacle located at x=o. The flow field has fore-aft symmetry about the obstacle. Recall, h is defined as the distance from the obstacle centerline a particle shifts to after encountering that obstacle. With the present assumptions, the shift is the result of physical contact, so only flow streamline information and particle size are needed to find h. The analysis is carried out in a non-dimensional form and the dimensions are normalized by the obstacle radius. Therefore, the non-dimensional shift, h, is a function of the Reynolds number, Re, and relative particle diameter, d where d=particle diameter divided by obstacle radius. The influence of particle size on h is shown as a function of Re in FIG. 3. As can be seen the shift increases as the relative particle size increases and as the Reynolds number increases. The strong dependence of h on the particle size is clearly shown in FIG. 4. These results demonstrate that increasing the relative particle size (or decreasing the obstacle size) increases the particle shift obtained. Increasing the Reynolds number, which is proportional to the suspending fluid velocity, also increases h.

Therefore, for an OIPD device, the obstacle Re should be as large as possible without creating unsteady vortex shedding. The particle diameter to obstacle ratio should also be made as large as possible. The obstacle size will probably be limited by the device fabrication techniques. Obstacle diameters of the same order of magnitude as the particles should be used. Glass, metal or synthetic fibers such as polyester may form the obstacles and are readily available with diameters of a few microns or less. The OIPD process is most easily implemented with particles greater than 0.1 micron in diameter. If surface characteristics or particle charge is used to alter the shift h then the sizes may be much smaller. Devices for much larger particles, say greater than a few millimeter, may also be easily implemented.

Particular embodiments of devices that may be used to implement the OIPD process will now be described. As discussed, it was discovered that by providing a non-uniform obstacle field the net shift in path of the particles could be controlled and directed in a specific direction.

Figure 5:
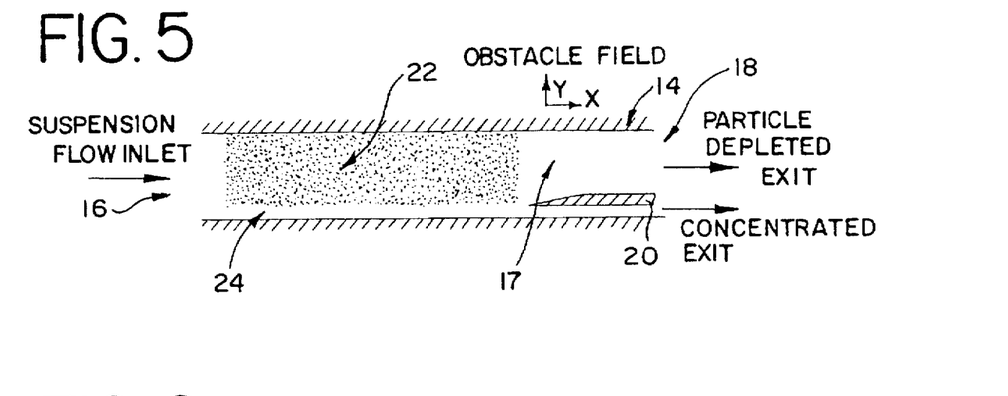
FIG. 5 illustrates a cross-sectional view of an apparatus used to perform OIPD according to a first preferred embodiment of the present invention taken along the suspension flow direction.

FIG. 5 illustrates a cross-sectional view of an apparatus used to perform OIPD according to a first preferred embodiment of the present invention taken along the suspension flow direction. The apparatus includes a conduit or a duct 14 preferably having a cross section rectangular in shape. The duct 14 has an inlet 16 and an outlet 18 and an inner lumen 17 extending from the inlet to the outlet. The inlet 16 is coupled to a source of fluid having particles suspended therein (not shown). A splitter plate 20 near the outlet 18 of the duct 14 divides the outlet into two outlets so that the concentrated particles and the particle depleted solution can be separately collected. An obstacle field 22 is located in the interior of the duct 14 between the inlet 16 and outlet 18 of the duct. In a preferred embodiment, the obstacle field 22 is formed by a collection of randomly oriented fibers separated sufficiently to avoid trapping particles. The obstacle field 22 is uniform on one side of the duct 14 and absent on the other thereby creating a step in the spatial density across the duct 14 or a non-uniform obstacle field. The depth of the obstacle free region 24 of the duct is kept relatively small to keep the flow velocity more uniform across the duct.

A rough estimate of dimensions of the apparatus that may be suitable to separate particles with a diameter of 8 microns (μm) are as follows:

obstacle field height: 0.4 cm
obstacle free region height: 0.1 cm
obstacle field length: 40 cm
obstacle diameters: 4 μm
spatial obstacle density: 625 obstacles/mm$^2$ It is estimated that an apparatus having such dimensions should yield a concentrated exit concentration of approximately five times the inflow suspension concentration. Of course, these dimensions would not be suitable for large scale production applications.

Figure 5A:
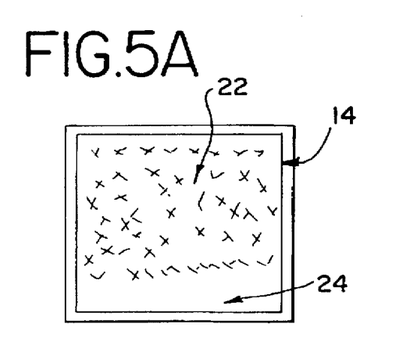
FIG. 5A illustrates cross-sectional view of the apparatus shown in FIG. 5.

FIG. 5A illustrates a cross-sectional view of the apparatus shown in FIG. 5.

The obstacle field can be implemented in a number of various ways. For example, the obstacle field can be created from a random collection of fibers, or a series of screen or mesh material, coiled or folded mesh, individually placed fibers or rods and possibly a porous material having interconnecting compartments large enough for the particles to pass therethrough without being trapped. A variety of methods may be used to secure the obstacle field within the conduit. The simplest uses friction for force fitting of the obstacle matrix in the conduit. Adhesives may also be employed to secure the obstacle field in place. The obstacles may also be "potted" within the duct wall itself. In this case, the edges of the obstacles or obstacle matrix are embedded in a liquid wall material such as polyurethane; once in place, the wall material is allowed to cure. Another approach, useful for obstacle fields composed of a series of meshes placed perpendicular to the flow, sandwiches each mesh between thin washer-like sections of the duct wall.

In the embodiments described, prototypes were built and tested with a suspension of neutrally buoyant polystyrene spheres approximately 0.5 mm in diameter. The suspending fluid was a mixture of water, glycerine and detergent. The glycerin was added to match the solution density to that of the spheres. A detergent was added to prevent aggregation of the particles.

Figure 6:
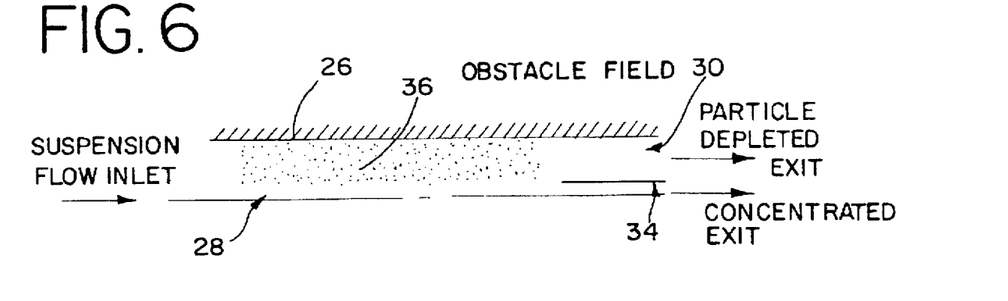
FIG. 6 illustrates a cross-sectional view of an apparatus used to perform OIPD according to a second preferred embodiment of the present invention taken along the suspension flow direction.

FIG. 6 illustrates a cross-sectional view of an apparatus used to perform OIPD according to a second preferred embodiment of the present invention taken along the suspension flow direction. Instead of a rectangular duct as shown in FIG. 5 with an obstacle free region along one side of the duct, a cylinder 26 is used. The apparatus has an axially symmetric configuration in which the center of the cylinder is obstacle free. Only one half of the cylinder 26 is illustrated, the center axis of the duct indicated by dashed line 28. A second cylinder 34 located at the outlet 30 divides the outlet 30 in two. The second cylinder 34 has a smaller diameter than cylinder 26 and is concentrically positioned with respect to cylinder 26. The center cylinder 34 collects the concentration of particle while the particle depleted fluid flows through the annular region between outer cylinder 26 and inner cylinder 34. In this preferred embodiment, the obstacle field 36 is created by a series of annular meshes. The holes in the mesh are large enough to allow the particles to pass therethrough. The obstacle field 36 is uniform across the cylinder 26 except along the center region of the cylinder which is obstacle free.

Figure 6A:
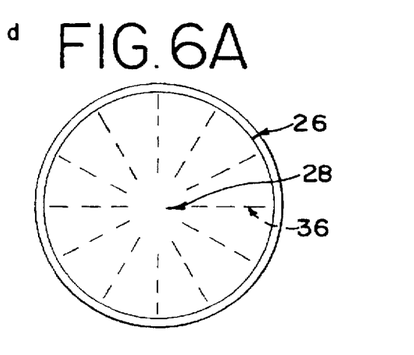
FIG. 6A illustrate a cross-sectional view of the apparatus shown in FIG. 6.

FIG. 6A illustrates a cross-sectional view of the apparatus shown in FIG. 6.

Figure 7:
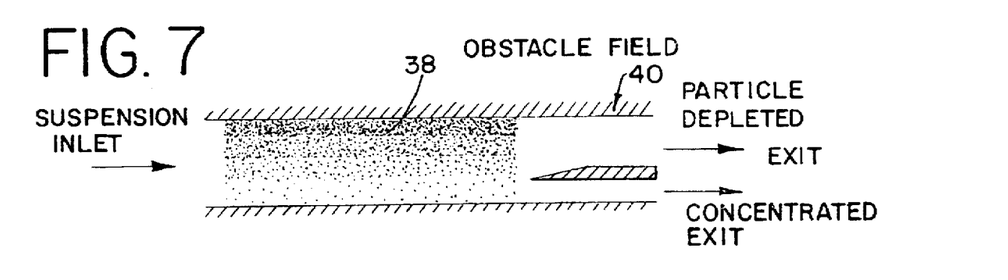
FIG. 7 illustrates a cross-sectional view of an apparatus used to perform OIPD according to a third preferred embodiment of the present invention taken along the suspension flow direction.
Figure 8:
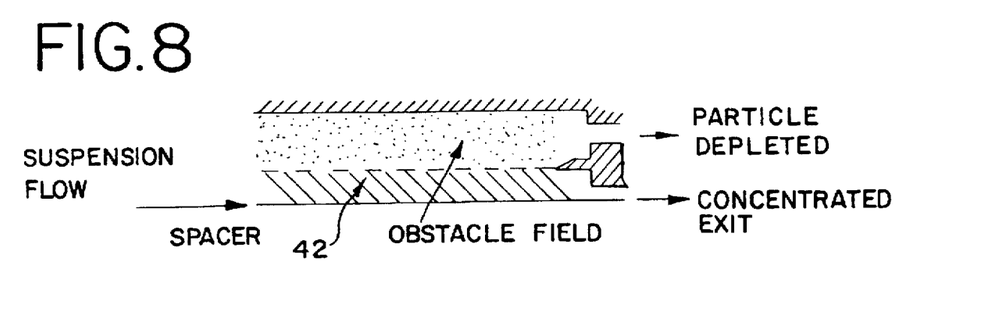
FIG. 8 illustrates a cross-sectional view of an apparatus used to perform OIPD according to a fourth preferred embodiment of the present invention taken along the suspension flow direction.
Figure 9:
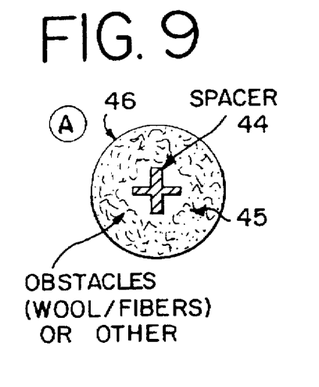
FIGS. 9–11 illustrate cross-sectional views of various apparatus taken perpendicularly to the suspension flow direction.
Figure 10:
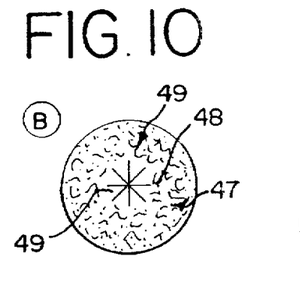
Figure 11:
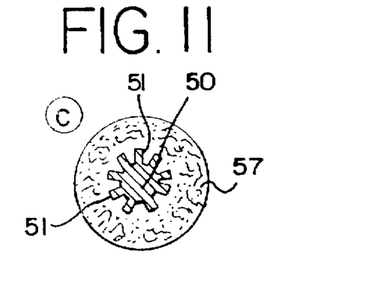
Figure 12:
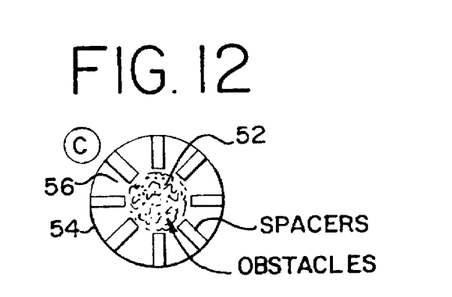
FIGS. 12–13 illustrate cross-sectional views of various apparatus taken perpendicularly to the suspension flow direction according to another preferred embodiment.
Figure 13:
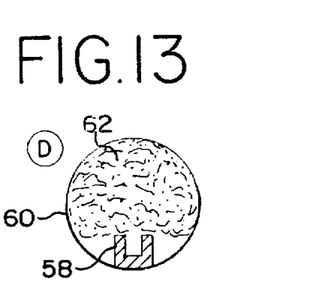

FIG. 7 illustrates a cross-sectional view of an apparatus used to perform OIPD according to a third preferred embodiment of the present invention taken along the suspension flow direction. The obstacle field 38 is similar to that previously described with reference to FIG. 6, however, the obstacle field 38 is created by parallel cylinders that traverse the cylinder 40. The spatial density of the obstacle field 38 varies in a direction perpendicular to the mean flow and perpendicular to the cylinder axis. In this preferred embodiment there is no obstacle free region rather the spatial density increases across the cross-section of the cylinder. While the apparatus shown in FIG. 7 is shown with a rectangular duct, it may also be implemented in an axially symmetrical configuration.

Figures 14, 15, 16:
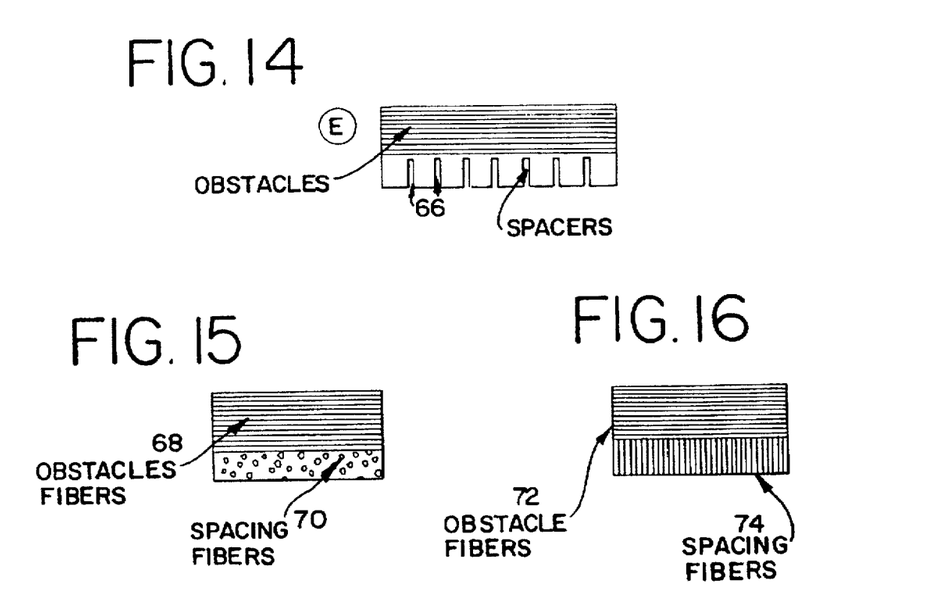
FIGS. 14–16 illustrate a cross-sectional view of a non-cylindrical duct having a spacer taken perpendicularly to the suspension flow direction.

The apparatus used to carry out the OIPD method results in preferential dispersion of particles by passing a fluid containing the particles through a field of obstacles which induce dispersion of the particles in a direction perpendicular to the fluid flow. By properly configuring the obstacles, the dispersion can be produced in a particular direction, i.e. the particles migrate in one direction perpendicular to the fluid flow. This preferential dispersion results in a non-uniform concentration of particles downstream of the obstacle field. By appropriate collection, a solution with increased or decreased particle concentration is obtained. The rate of migration of the particles is also dependent upon particle size. Thus, by providing various collection points along the fluid flow path, particles of different sizes can be extracted from the fluid at different points along the conduit.

FIG. 8 illustrates a cross-sectional view of an apparatus used to perform OIPD according to a fourth preferred embodiment of the present invention taken along the suspension flow direction. The apparatus shown in FIG. 8 is similar to that shown in FIG. 6 and thus the same reference numerals will be used to refer to similar elements. The apparatus of FIG. 8, however, includes a spacer 42 which occupies the center portion of the cylinder. As previously described the obstacle field may be produced by various methods. The spacer 42 may also have various configurations as will be described, however, one common requirement is that it must allow the radial migration of particles and some axial flow of the fluid in the obstacle free region. The spacer 42 serves two functions. First, the spacer 42 slows the flow velocity in the obstacle free region and therefore enhances the obstacle induced preferential dispersion. Secondly, if flexible fibers are used for the obstacle field, the spacer 42 maintains the obstacle free region.

FIGS. 9–11 illustrate cross-sectional views of various apparatus taken perpendicularly to the suspension flow direction. FIGS. 9–11 illustrate various configurations of a spacer and obstacle field that may be used with the apparatus shown in FIG. 8. In FIGS. 9–11 the flow of the particle containing fluid is out of the page. In FIG. 9, the spacer 44 has a cross configuration thereby dividing the center portion of the duct 46 into quadrants. In FIG. 10 the spacer 48 has a plurality of webs 49. While eight radial webs are shown the number of webs can be changed and the present invention is not limited to this particular illustration. In FIG. 11 the spacer 50 has a solid cylindrical center region with short webs 51 extending radially therefrom. In the preferred embodiments shown in FIGS. 9–11 the spacers 44, 48 and 50, respectively, extend along the longitudinal axis of the duct and the obstacle fields 45, 47 and 52 are located in the annular region between the conduit and the spacers.

Alternatively, the position of the obstacle field and the obstacle free region or spacer may be reversed. FIGS. 12 and 13 illustrate such embodiments. In FIG. 12 the obstacle field 52 is in the center of the duct 54 and the spacer 56 is located in the annular region surrounding the obstacle field 52. In FIG. 13 the spacer 58 has a U-shaped channel cross section and is located at the bottom of the duct 60 and the obstacle field 62 fills the remainder of the duct 60 cross-section. In this preferred embodiment, the collection outlet (not shown) would be asymmetrical of course whereas in the embodiments illustrated in FIGS. 6 and 8–12 the collection outlet is symmetrical with respect to the duct axis.

While the spacers embodied in FIGS. 9–13 were used with ducts having circular cross sections, spacers may also be used with non-circular ducts such as that illustrated in FIGS. 5 and 7. FIGS. 14–16 illustrate a cross-sectional view of a non-cylindrical duct having a spacer taken perpendicularly to the suspension flow direction. In FIGS. 14–16 the flow of fluid is out of the page. In FIG. 14 the spacer 64 has slots 66 extending perpendicularly to the direction of fluid flow and parallel to the direction of particle migration. In FIG. 15 the obstacle field 68 is preferably formed by fibers and the spacer 70 is created from the same fibers. In particular, the fibers forming the spacer 70 extend in a direction parallel to the fluid flow and perpendicularly to the direction of particle migration. In FIG. 16, the obstacle field 72 is also preferably formed of fibers and the same fibers are used to create the spacer 74. The fibers forming the spacer 74 in this preferred embodiment are aligned perpendicularly to the direction of fluid flow and parallel to the direction of particle migration.

The spacers shown in FIGS. 9-14 may be formed of plastic to have the desired shape. The spacers could also be machined, molded or extruded from other materials such as glass or metal, for example.

Figure 17:
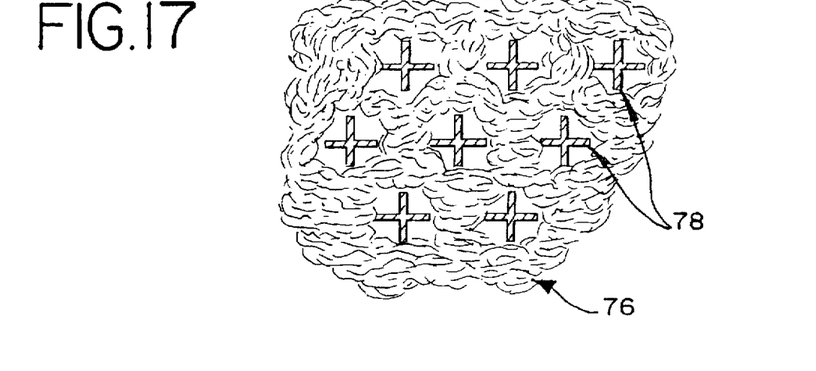
FIG. 17 illustrates a cross-sectional view of an apparatus having multiple obstacle fields and spacers taken perpendicularly to the suspension flow direction.

While the previous embodiments have described single distribution systems having one collection output, the OIPD system of the present invention can also be used with distributed collection systems. FIG. 17 illustrates a cross-sectional view of a duct (not shown) having multiple obstacle fields 76 and spacers 78 taken perpendicularly to the suspension flow direction. Flow of the particle suspending fluid is out of the page. With such a distribution system multiple collection outlets (not shown) must be provided.

Figure 18:
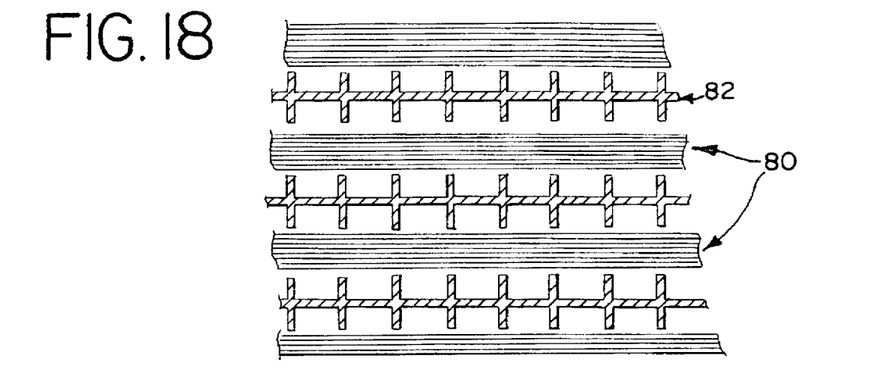
FIG. 18 illustrates a cross-sectional view of another preferred embodiment of a distributed collection system taken perpendicularly to the suspension flow direction.
Figure 19:
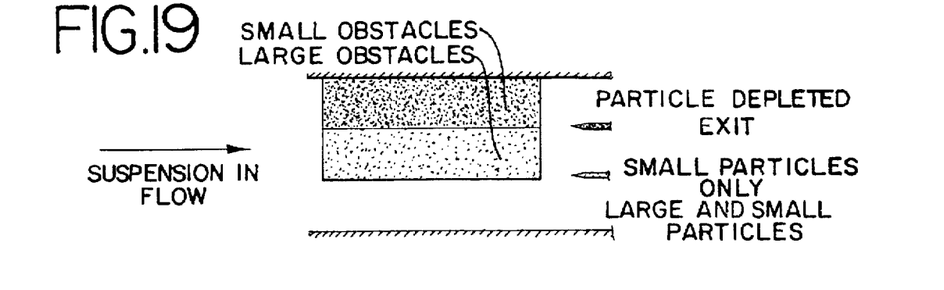
FIGS. 19 and 20 illustrate a cross-sectional view of apparatus used to stratify particles of different sizes taken along the fluid suspension flow direction.
Figure 20:
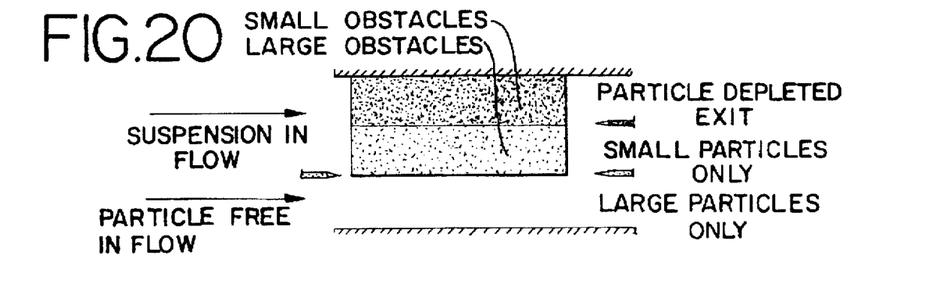
Figure 21:
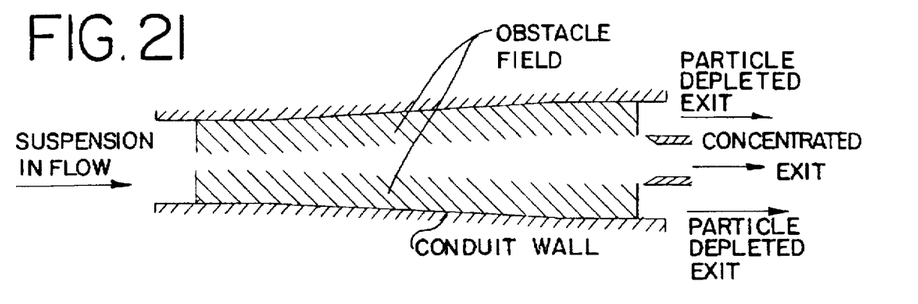
FIG. 21 illustrates a cross-sectional view of an apparatus having a varying channel cross section taken along the fluid suspension flow direction.
Figure 22:
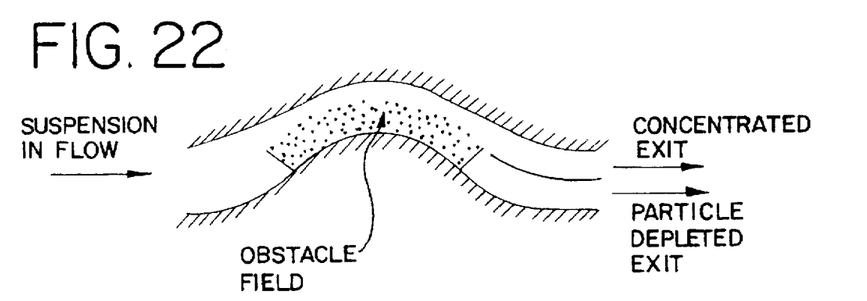
FIG. 22 illustrates a cross-sectional view of an apparatus used to create a velocity gradient within the obstacle field taken along the fluid suspension flow direction.
Figure 23:
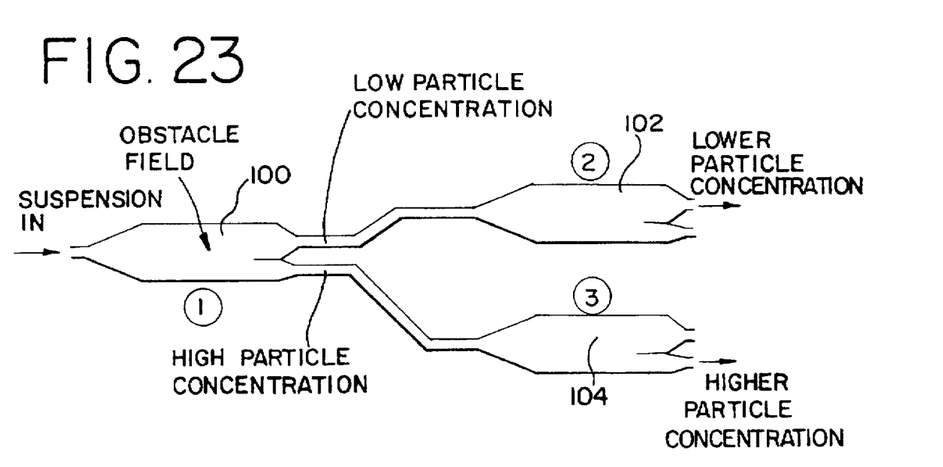
FIG. 23 illustrates a cross-sectional view of multiple cascaded devices used to enhance particle concentration/depletion taken along the fluid suspension flow direction.

FIG. 18 illustrates a cross-section view of another preferred embodiment of a distributed collection system according to the present invention taken perpendicularly to the suspension flow direction. In this embodiment, the duct (not shown) is divided into bands of obstacle fields 80 alternating with band of spacers 82. The obstacle fields 80 can be formed by fibers extending in the direction perpedicular to the fluid flow.

Thus far, only apparatus having conduits with uniform cross sections along the length of the conduit have been discussed. Devices with non-uniform cross sections may be more effective. As the separation process progresses down the length of a device, the local suspension concentrations will change resulting in effective suspension viscosity variations. Non-uniform channel cross sections may compensate for these variations. One such device is shown in FIG. 21. Furthermore non-uniform configurations may be used to create velocity gradients perpendicular to the flow for enhancing separation, see the second term in equation (1). One possible device to achieve this is shown in FIG. 22. The curvature of the wall next to the obstacle field will create a velocity gradient within the obstacle field that can enhance the OIPD process.

While it was assumed that the OIPD process was performed using dilute suspensions, the process should also be effective at high particle concentrations. The apparatus details for high particle concentrations may have to be altered, but the basic process is still applicable.

Multiple cascaded devices may be required to achieve desired particle depleted and particle rich suspension concentrations. FIG. 23 illustrates such an arrangement. Such a cascaded arrangement enhances the particle concentrating/depleting effects. A similar arrangement could be used to separate or stratify a solution with multiple particle sizes. In order to stratify a solution with multiple particle sizes, the obstacle fields 100, 102 and 104 would have different characteristics, for example, the size of the obstacles in each field may be different, or they may be charged differently. These devices do not exclude particles—OIPD is a diffusion process so it does not guarantee a solution void of particles (a very small concentration may be left). In addition, a series of devices with different characteristics (obstacle size etc.) may be useful for separation of suspensions containing multiple particle sizes. For example, a series of devices could be designed to remove successively smaller particles.

A cascaded arrangement would not be required for stratifying multiple particle sizes. Because the particle shift, h, is dependent on the particle size relative to the obstacle size, a device with several fields containing different obstacle sizes could stratify a mixture of particle sizes. Two configurations are shown in FIGS. 19 and 20. For simplicity, consider a suspension of small and large particles. Large obstacles would shift the larger particles, but would not have much effect on smaller particles, see the derived relation between h and obstacle diameter shown in FIG. 3. Recall the particle flux normal to the flow direction is a very strong function of h, so larger obstacles would produce virtually no flux of smaller particles. The smaller obstacles in FIGS. 19 and 20 would be able to shift the smaller particles and drive the separation of both the small and large particles. The first device shown in FIG. 19 would not have an outflow containing solely large particles. The second device shown in FIG. 20 remedies this by adding a particle free inflow in an obstacle free region. This region would only contain particles that migrated there by the particle shift, and would exit containing only large particles. Similarly, stratification of differently charged particles or particles with different surface properties could be achieved with regions of differently charged obstacles or regions of obstacles with different surface properties.

Of course, it should be understood that a wide range of changes and modifications can be made to the preferred embodiments described above. It is therefore intended that the foregoing detailed description be regarded as illustrative rather than limiting and that it be understood that it is the following claims, including all equivalents, which are intended to define the scope of this invention.

What is claimed is:

1. An apparatus for dispersing particles suspended in a fluid, the apparatus comprising:

a conduit having an inlet, an outlet and an inner lumen extending from said inlet to said outlet; and a non-uniform obstacle field disposed in said inner lumen of said conduit, said non-uniform field having a configuration that causes said particles suspended in the fluid to disperse in a differential manner in a direction perpendicular to the flow of fluid as it flows through said conduit.

2. An apparatus according to claim 1 wherein said non-uniform obstacle field is formed by a collection of fibers.

3. An apparatus according to claim 1 wherein said non-uniform obstacle field is formed by a collection of rods.

4. An apparatus according to claim 1 wherein said non-uniform field is formed by a mesh.

5. An apparatus according to claim 1 wherein said inner lumen of said conduit is divided into a top portion and a bottom portion wherein said non-uniform obstacle field is present in said top portion but is absent in said bottom portion to create an obstacle free region in said bottom portion.

6. An apparatus according to claim 5 further comprising a spacer disposed in said bottom portion of said inner lumen.

7. An apparatus according to claim 1 wherein said inner lumen of said conduit is divided into a center section and an annular outer section wherein said non-uniform obstacle field is present in said outer annular section and absent in said center section.

8. An apparatus according to claim 7 further comprising a spacer is disposed in said center portion of said lumen.

9. An apparatus according to claim 1 wherein said inner lumen of said conduit is divided into a center section and an annular outer section wherein said non-uniform obstacle field is present in said center section and is absent in said outer annular section.

10. An apparatus according to claim 9 further comprising a spacer disposed in said outer annular section.

11. An apparatus according to claim 1 wherein said non-uniform obstacle field has surface properties which alter the dispersion of particles.

12. An apparatus according to claim 1 wherein said non-uniform obstacle field is formed by charged obstacles to alter the dispersion of particles suspended in the fluid.

13. An apparatus according to claim 12 wherein said obstacle field is formed by magnetically charged obstacles.

14. An apparatus according to claim 12 wherein said obstacle field is formed by electrically charged obstacles.

15. An apparatus according to claim 1 further comprising at least a second conduit having an inlet, an outlet and an inner lumen extending from said inlet to said outlet;

said conduit having a non-uniform obstacle field disposed in said inner lumen of said conduit wherein said inlet of said second conduit is coupled to said outlet of said conduit.

16. An apparatus according to claim 1 wherein said non-uniform obstacle field is formed by a porous media.

17. A method for dispersing particles suspended in a fluid comprising the steps of:

providing a conduit having an inlet, an outlet and an inner lumen extending from said inlet to said outlet;

providing a non-uniform obstacle field in a portion of said conduit;

injecting a fluid having particles suspended therein in said inlet of said conduit; and collecting said particles at said outlet of said conduit.

18. A method according to claim 17 further comprising the step of disposing said non-uniform obstacle field in said inner lumen wherein a portion of said inner lumen is obstacle free.

19. A method according to claim 18 further comprising the step of disposing a spacer in said obstacle free region.

20. A method for separating particles from a particle entrained fluid, the method comprising the steps of:

directing said fluid to flow though a conduit having an inlet, an outlet and an inner lumen extending from said inlet to said outlet; and dispersing the particles in a direction perpendicular to the direction of fluid flow through said conduit to create a particle depleted region at said outlet of said conduit.

21. A method according to claim 20 wherein said step of dispersing the particles is accomplished by providing a non-uniform obstacle field in a portion of said conduit.

22. A method according to claim 21 further comprising the step of collecting the dispersed particles at said outlet of said conduit.

23. A method according to claim 21 further comprising the step of providing a spacer in said inner lumen of said conduit not occupied by said non-uniform obstacle field.

24. An apparatus for dispersing particles suspended in a fluid, the apparatus comprising:

a receptacle for receiving the fluid having particles suspended therein; and a first obstacle field disposed in the receptacle, the obstacle field having a configuration that causes the particles suspended in the fluid to disperse in a differential manner in a direction perpendicular to the flow of fluid as it flows through the receptacle.

25. An apparatus according to claim 24 wherein the dispersion of particles is dependent upon the particles' characteristics.

26. An apparatus according to claim 24 wherein the dispersion of particles includes separating the particles based upon the particles' characteristics.

27. An apparatus according to claim 24 wherein the dispersion of particles includes stratifying the particles based upon the particles' characteristics.

28. An apparatus according to claim 24 wherein the dispersion of particles includes concentrating the particles based upon the particles' characteristics.

29. An apparatus according to claim 24 further comprising at least two collection locations for collecting the dispersed particles.

30. An apparatus according to claim 24 further comprising at least one inlet for receiving a particle-free fluid.

31. An apparatus according to claim 24 wherein portion of the receptacle is obstacle free.

32. An apparatus according to claim 31 further comprising a spacer disposed in the portion of the receptacle that is obstacle free.

33. An apparatus according to claim 24 further comprising a velocity gradient in the receptacle.

34. An apparatus according to claim 33 wherein the velocity gradient is controlled by the shape of the receptacle.

35. An apparatus according to claim 33 wherein the velocity gradient is controlled by the configuration of the obstacle field.

36. An apparatus according to claim 24 wherein the receptacle has at least one inlet and at least one outlet.

37. An apparatus according to claim 24 wherein the first obstacle field is non-uniform.

38. An apparatus according to claim 24 wherein the first obstacle field is uniform.

39. An apparatus according to claim 24 wherein the first obstacle field is formed by a collection of fibers.

40. An apparatus according to claim 24 wherein the first obstacle field is formed by a collection of rods.

41. An apparatus according to claim 24 wherein the first obstacle field is formed by a mesh.

42. An apparatus according to claim 24 wherein the first obstacle field is formed by a porous media.

43. An apparatus according to claim 24 wherein the first obstacle field is formed by obstacles having surface properties which alter the dispersion of particles.

44. An apparatus according to claim 24 wherein the first obstacle field is formed by charged obstacles.

45. An apparatus according to claim 44 wherein the obstacles are magnetically charged.

46. An apparatus according to claim 44 wherein the obstacles are electrically charged.

47. An apparatus according to claim 24 further comprising a plurality of obstacle fields disposed in the receptacle.

48. An apparatus according to claim 47 wherein each of the plurality of obstacle fields has a different characteristic from each of the other plurality of obstacle fields.

49. An apparatus according to claim 47 wherein the plurality of obstacle fields are asymmetrically disposed in the receptacle.

50. An apparatus according to claim 47 wherein the plurality of obstacle fields are symmetrically disposed in the receptacle.

51. An apparatus according to claim 47 wherein the plurality of obstacle fields are sequentially disposed in the receptacle so that the fluid will flow through one obstacle field at a time.

52. An apparatus according to claim 24 wherein said obstacle field is formed by a plurality of obstacles of different size.

53. An apparatus according to claim 24 wherein said obstacle field is formed by a plurality of obstacles of different shape.

54. An apparatus according to claim 24 wherein the receptacle is a conduit having two inlets wherein one of the inlets receive a fluid substantially free of particles and the other inlet receives a fluid having particles entrained therein and the conduit having three outlets and an inner lumen extending from the two inlets to the three outlets, the apparatus further comprising a second obstacle field disposed in the receptacle wherein the second obstacle field has a different characteristic than the first obstacle field.

55. An apparatus according to claim 54 wherein the second obstacle field is disposed on top of the first obstacle field in an upper portion of the inner lumen and the second obstacle field is formed by obstacles smaller in size than the first obstacle field.

56. An apparatus according to claim 24 further comprising a second obstacle field disposed in the receptacle wherein the second obstacle field has an orientation that is different from the first obstacle field.

57. An apparatus according to claim 24 further comprising at least a second receptacle having a second obstacle field disposed therein wherein the second receptacle is coupled to the first receptacle.

58. A method for dispersing particles suspended in a fluid comprising the steps of:

providing a receptacle for receiving the fluid having particles suspended therein;

providing an obstacle field in at least a portion of the receptacle;

causing a fluid having particles suspended therein to flow through the obstacle field wherein the obstacle field causes the particles to disperse in a differential manner in a direction perpendicular to the flow of fluid.

59. A method according to claim 58 further comprising the step of separating the particles at different locations in the receptacle.

60. A method according to claim 58 further comprising the step of stratifying the particles.

61. A method according to claim 58 further comprising the step of concentrating the particles.

62. A method according to claim 58 wherein the obstacle field is formed by a plurality of charged obstacles.

63. A method according to claim 62 wherein the obstacles are magnetically charged.

64. A method according to claim 62 wherein said obstacles are electrically charged.

65. A method according to claim 58 wherein the obstacle field is formed by obstacles having surface properties which alter the dispersion of particles.

* * * * *

UNITED STATES PATENT AND TRADEMARK OFFICE
CERTIFICATE OF CORRECTION

PATENT NO.    :    5,715,946
DATED         :    February 10, 1998
INVENTOR(S)   :    Steven H. Reichenbach It is certified that error appears in the above-identified patent and that said Letters Patent is hereby corrected as shown below:

In claim 20, line 3, change "though" to --through--.

Signed and Sealed this

Second Day of May, 2000

Attest:

Q. TODD DICKINSON

*Attesting Officer*     *Director of Patents and Trademarks*